United States Patent [19]
Ghahramani

[11] Patent Number: 6,139,152
[45] Date of Patent: Oct. 31, 2000

[54] ELECTRONIC DEPTH PERCEPTION TESTING SYSTEM AND APPARATUS FOR CONDUCTING DEPTH PERCEPTION TESTS

[76] Inventor: Bahador Ghahramani, 728 Republic Dr., Rolla, Mo. 65409

[21] Appl. No.: 09/514,788

[22] Filed: Feb. 28, 2000

[51] Int. Cl.⁷ .................................................. A61B 3/02
[52] U.S. Cl. ........................................................ 351/243
[58] Field of Search ................................. 351/201, 202, 351/213, 200, 222, 233, 240, 243, 245, 224

[56] References Cited

U.S. PATENT DOCUMENTS

| | | | |
|---|---|---|---|
| 4,260,226 | 4/1981 | Ghahramani | 351/3 |
| 4,464,027 | 8/1984 | Cooper | 351/203 |
| 4,506,963 | 3/1985 | Cooper | 351/203 |
| 5,357,293 | 10/1994 | Uomori et al. | 351/209 |
| 5,801,666 | 9/1998 | Mac Farlane | 345/6 |
| 5,825,456 | 10/1998 | Tabata et al. | 351/201 |
| 5,864,384 | 1/1999 | McClure et al. | 351/224 |
| 5,877,840 | 3/1999 | Yamada et al. | 351/201 |
| 5,888,074 | 3/1999 | Stapin et al. | 434/258 |
| 5,898,474 | 4/1999 | McClure et al. | 351/224 |
| 5,910,834 | 6/1999 | McClure et al. | 351/224 |
| 5,929,572 | 7/1999 | Whitesell | 315/169.3 |

*Primary Examiner*—George Manuel
*Attorney, Agent, or Firm*—Richard L. Marsh

[57] ABSTRACT

An electronic eye depth testing method comprises a three dimensional cubic space displayed on a display screen, wherein the cubic space has a first image of a three dimensional object and a second image of a three dimensional object randomly placed within the cubic space. The first image is located at the intersection of two perpendicular horizontal planes and a vertical plane perpendicular to said two horizontal planes and the second image is located at the intersection of two perpendicular horizontal planes and a vertical plane perpendicular to said two horizontal planes. A subject to be tested for depth perception is directed to move the images into convergence in the center of the cubic space.

20 Claims, 6 Drawing Sheets

ELECTRONIC DEPTH PERCEPTION TESTING SYSTEM AND APPARATUS FOR CONDUCTING DEPTH PERCEPTION TESTS

BACKGROUND OF THE INVENTION

1. Field of the Invention

This invention relates to an electronic testing method for eye depth perception. The testing method comprises a three dimensional cubic space displayed on a display screen, wherein a subject to be tested moves a first image of a three dimensional object and a second image of a three dimensional object into convergence in the center of the cubic space. The first and second images are randomly placed within the cubic space wherein and may further comprise identical or differing objects of similar or differing color or of similar or differing shape.

2. Prior Art Statement

Study and work in the field of eye disorders has produced a plethora of devices and methods to measure the various disorders and/or to assist in training of the eyes to enhance performance. Depth perception is the ability to judge the relative spatial alignment of objects whereas vision is defined as an ability to see an object. Thus, a person may have 20/20 vision yet lack good depth perception. Persons in hazardous occupations and those charged with the safe delivery of passengers require excellent depth perception as well as excellent vision. For instance, air line pilots must have both abilities in order to safely land an aircraft on a plane surface from aloft in a cubic space. Similar characteristics are required of bus drivers, construction personnel, crane and forklift operators. Of course, all persons benefit from good vision and proper depth perception.

It is known to provide a mechanical device to test for depth perception by providing a pair of objects in carriers in elongated slots in the lid of an enclosure wherein a subject to be tested uses a loop to move both objects simultaneously toward or away from each other wherein the color, distance, cross-section, size of the pegs and the illumination may be manually changed. Mirrored walls are also provided to reflect the image of the pegs. For instance, see the U.S. Pat. No. 4,260,226 issued on Apr. 07, 1981, to Bahador Ghahramani.

It is also known to provide a mechanical device for testing, exercising and enhancing binocular vision by having a first stationary element oriented in a vertical plane equidistant from both eye apertures, a second stationary element oriented in the same vertical plane and spaced from the first element, a focus element in the same vertical plane as the stationary elements and means to move the focus element back and forth in the vertical plane from above one stationary element to above the other element. For instance, see the U.S. Pat. No. 4,464,027 and 4,506,963 issued on Aug. 7,1984 and Mar. 26, 1985, respectively, to Clifford W. Cooper.

It is further known to analyze depth perception by presenting a target on a first screen, detecting eye movement using the limbus reflection method from spectacle mounted eye detectors, removing the saccade component and calculating an amplitude of the vergence eye movement, change in convergence angle and cross-correlation of velocity or acceleration of left & right eye movement. For instance, see U.S. Pat. No. 5,357,293 issued on Oct. 18, 1994 to Uomori, et al.

Additionally, it is known to measure stereoscopic convergence using an eye-point camera in a head worn apparatus to detect movement of the eyeball when a virtual image of an object is moved in one eyepiece relative to a fixed virtual image in the other eyepiece. For instance, see the U.S. Pat. No. 5,825,456 issued on Oct. 20, 1998 to Tabata, et al.

It is also known to provide a virtual reality apparatus for testing, measuring and quantifying information from head gear worn by a subject being tested. The head gear has an excitation device for supplying a test stimuli to a screen in the foreground of the head gear, a feed back device operated by the subject to respond to the test stimuli, a computer for receiving, interpreting, sequencing and sending information to the subject and a printing device to supply a permanent record. For instance, see the U.S. Pat. No. 5,864,384 and 5,898,474 and 5,910,834 issued on Jan. 26, 1999, Apr. 27, 1999 and Jun. 8, 1999, respectively, to McClure, et al.

It is still further known to provide a binocular view function inspecting apparatus comprising a display for displaying a reference image and an index image in three dimensional spatial relationship, an input device for a test subject to move the display position of the index image in order that a predetermined reference position of the reference image and the display position of the index image coincide, a second input device for the test subject to confirm the coincidence of the images and a calculation to determine the amount of deviation of the index image from the reference position. For instance, see the U.S. Pat. No. 5,877,840 issued on Mar. 2, 1999 to Yamada, et al.

It is also known to provide a system for testing and evaluating driver situational awareness comprising a computer for generating and displaying road and traffic images, displaying instruction data, receiving response data from a subject, measuring response signals & times and providing an output of the results. For instance, see the U.S. Pat. No. 5,888,074 issued on Mar. 30, 1999 to Stapin, et al.

Finally, it is known to provide a display for providing physiological depth cues for true 3-D imaging which comprises a cubic matrix of substantially transparent material having an array of voxels of electroluminescent material arranged in the matrix activated by a plurality of substantially transparent electrodes operably coupled to the array of voxels. For instance, see the U.S. Pat. No. 5,929,572 issued on Jul. 27, 1999 to Eric James Whitesell.

SUMMARY OF THE INVENTION

The apparatus described in the aforementioned U.S. Pat. No. 4,260,226 commonly owned by the inventor of the instant invention was useful in a fixed location however, was difficult to move and hence was not readily utilized in multiple locations. The range of peg colors, shapes and sizes was limited to the locations fixed on the carriers in the box and further was limited by space between the carriers. Furthermore, the carriers were movable only toward and away from the subject thereby providing only linear perception of depth. Statistics gathered utilizing the mechanical device provided only rankings of linear depth perception for the ninety six possible different combinations of four distances from the box, three colors of pegs, four levels of illumination and two distances between pegs. Therefore, there is a need for an electronic eye depth testing method and apparatus comprising a three dimensional cubic space displayed on a display screen, wherein the cubic space has a first image of a three dimensional object and a second image of a three dimensional object, the first and second images randomly placed within the cubic space and wherein the first image is located at the intersection of two perpendicular vertical planes and a horizontal plane perpendicular to the two vertical planes, the second image located at the intersection of two perpendicular vertical planes and a horizontal plane perpendicular to the two vertical planes, wherein a subject to be tested moves the images into convergence in the center of the cubic space.

It is therefore an object of this invention to provide an electronic eye depth testing method and apparatus comprising a three dimensional cubic space displayed on a display screen, the cubic space having a first image of a three dimensional object and a second image of a three dimensional object, the first and the second images randomly placed within the cubic space wherein a subject to be tested moves the two images into convergence in the center of the cubic wherein the first image is initially located at the intersection of two perpendicular vertical planes and a horizontal plane perpendicular to the vertical planes, and the second image is initially located at the intersection of two perpendicular vertical planes and a horizontal plane perpendicular to the vertical planes.

It is yet another object of this invention to provide an electronic eye depth testing method and apparatus comprising a three dimensional cubic space displayed on a display screen, the cubic space having a series of horizontal planes extending through the side walls and through the rear wall and the front wall, a first series of vertical planes extending through the rear wall and front walls and through the top and bottom walls, and a second series of vertical planes extending through the bottom and top walls and the side walls of the cubic space.

Yet another object of this invention is to provide an electronic eye depth testing method and apparatus comprising a three dimensional cubic space displayed on a display screen having a first image of a three dimensional object and a second image of a three dimensional object randomly placed therewithin wherein the two images are moved simultaneously in opposite directions within one of the series of first planes using one pair of keys on a keyboard device used for controlling the images on the display screen, or simultaneously in opposite directions within one of the series of second planes using a second pair of keys or simultaneously in opposite directions within one of the series of third planes using a third pair of keys.

It is yet another object of this invention to provide an electronic eye depth testing method and apparatus comprising a three dimensional cubic space displayed on a display screen, the cubic space having a series of horizontal planes extending through the side walls and through the rear wall and the front wall, a first series of vertical planes extending through the rear wall and front walls and through the top and bottom walls, and a second series of vertical planes extending through the bottom and top walls and the side walls of the cubic space and wherein one of the two images is moved in a single direction in one of either of the series of vertical planes using a fourth pair of keys and/or moved in a single direction in one of series of the horizontal planes using a fifth pair of keys.

Still another object of this invention is to provide an electronic eye depth testing method and apparatus comprising a three dimensional cubic space displayed on a display screen having a first image of a three dimensional object and a second image of a three dimensional object randomly placed therewithin wherein the cubic space has a vertical axis, a first horizontal axis and a second horizontal axis, the vertical axis and the first and second horizontal axes crossing as the center of the cubic space and wherein the cubic space may be rotated about the first horizontal axis by a sixth set of keys on the keyboard and/or rotated about the vertical axis by a seventh set of keys on the keyboard.

An additional object of this invention is to provide an electronic eye depth testing method and apparatus comprising a three dimensional cubic space displayed on a display screen, the cubic space having a first image of a three dimensional object and a second image of a three dimensional object, the first and the second images randomly placed within the cubic space wherein a subject to be tested moves the two images into convergence in the center of the cubic space wherein the first image and the second image are of like color selected from the 256 ASCII colors and/or are of like shape and/or wherein the first image may be identical to the second image.

Yet an additional object of this invention is to provide an electronic eye depth testing method and apparatus comprising a three dimensional cubic space displayed on a display screen having a first image of a three dimensional object and a second image of a three dimensional object randomly placed therewithin wherein the cubic space has a vertical axis, a first horizontal axis and a second horizontal axis, the cubic space further having a reflective surface on at least one horizontal wall parallel to the second horizontal axis and the vertical axis, and/or a reflective surface on the rear wall parallel to the first horizontal axis and the vertical axis, and/or a reflective surface on the top and/or the bottom wall parallel to the first and second horizontal axes.

Still yet another object of this invention is to provide an electronic eye depth testing method and apparatus comprising a three dimensional cubic space displayed on a display screen having a first image of a three dimensional object and a second image of a three dimensional object randomly placed therewithin wherein the cubic space has a vertical axis, a first horizontal axis and a second horizontal axis, the cubic space further having a reflective surface on at least one horizontal wall or at least one vertical wall wherein the first image is reflected from each reflective surface and the second image is reflected from each reflective surface in a position relative to the first image and the second image respectively.

Still another object of this invention is to provide an electronic eye depth testing method and apparatus comprising a three dimensional cubic space displayed on a display screen having a first image of a three dimensional object and a second image of a three dimensional object randomly placed therewithin wherein the cubic space has a vertical axis, a first horizontal axis and a second horizontal axis wherein the cubic space may be rotated about the first horizontal axis and the vertical axis and wherein the cubic space further has a reflective surface on at least one horizontal wall and/or at least one vertical wall, wherein the first image is reflected from each reflective surface and the second image is reflected from each reflective surface in a position relative to the first image and the second image respectively and the reflections move with horizontal and/or vertical rotation of the cubic space relative to respective position of the first and second image.

Still another object of this invention is to provide an electronic eye depth testing method and apparatus comprising a three dimensional cubic space displayed on a display screen, the cubic space having a first image of a three dimensional object and a second image of a three dimensional object, the first and the second images randomly placed within the cubic space wherein a subject to be tested faces the space from position relative to front face and moves the images into convergence in the center of the cubic space by observing the first and second images through an open front wall of the cubic space.

Finally, it is an object of this invention to provide an electronic eye depth testing method and apparatus comprising a three dimensional cubic space displayed on a display screen having a first image of a three dimensional object and a second image of a three dimensional object randomly placed therewithin wherein the cubic space has a vertical axis, a first horizontal axis and a second horizontal axis, the vertical axis and the first and second horizontal axes crossing as the center of the cubic space and wherein the cubic space may be rotated about the first horizontal axis and/or rotated about the vertical axis wherein a subject to be tested faces the space from a position relative to front face and moves the images into convergence in the center of the cubic space by observing the first and second images through an open front wall of the cubic space wherein the front face aperture is reduced in size when the cubic space is rotated.

DESCRIPTION OF THE PREFERRED EMBODIMENTS

While the various features of this invention are hereinafter described and illustrated as an electronic eye depth testing method and apparatus comprising a three dimensional cubic space displayed on a display screen, the cubic space having a first image of a three dimensional object and a second image of a three dimensional object randomly placed within the cubic space wherein a subject to be tested moves the two images into convergence in the center of the cubic space, it is to be understood that the various features of this invention can be used singly or in various combinations thereof in an electronic eye depth testing method and apparatus comprising a three dimensional cubic space displayed on a display screen, the cubic space having a first image of a three dimensional object and a second image of a three dimensional object randomly placed within the cubic space wherein a subject to be tested moves the two images into convergence in the center of the cubic space as can hereinafter be appreciated from a reading of the following description.

Figure 1:
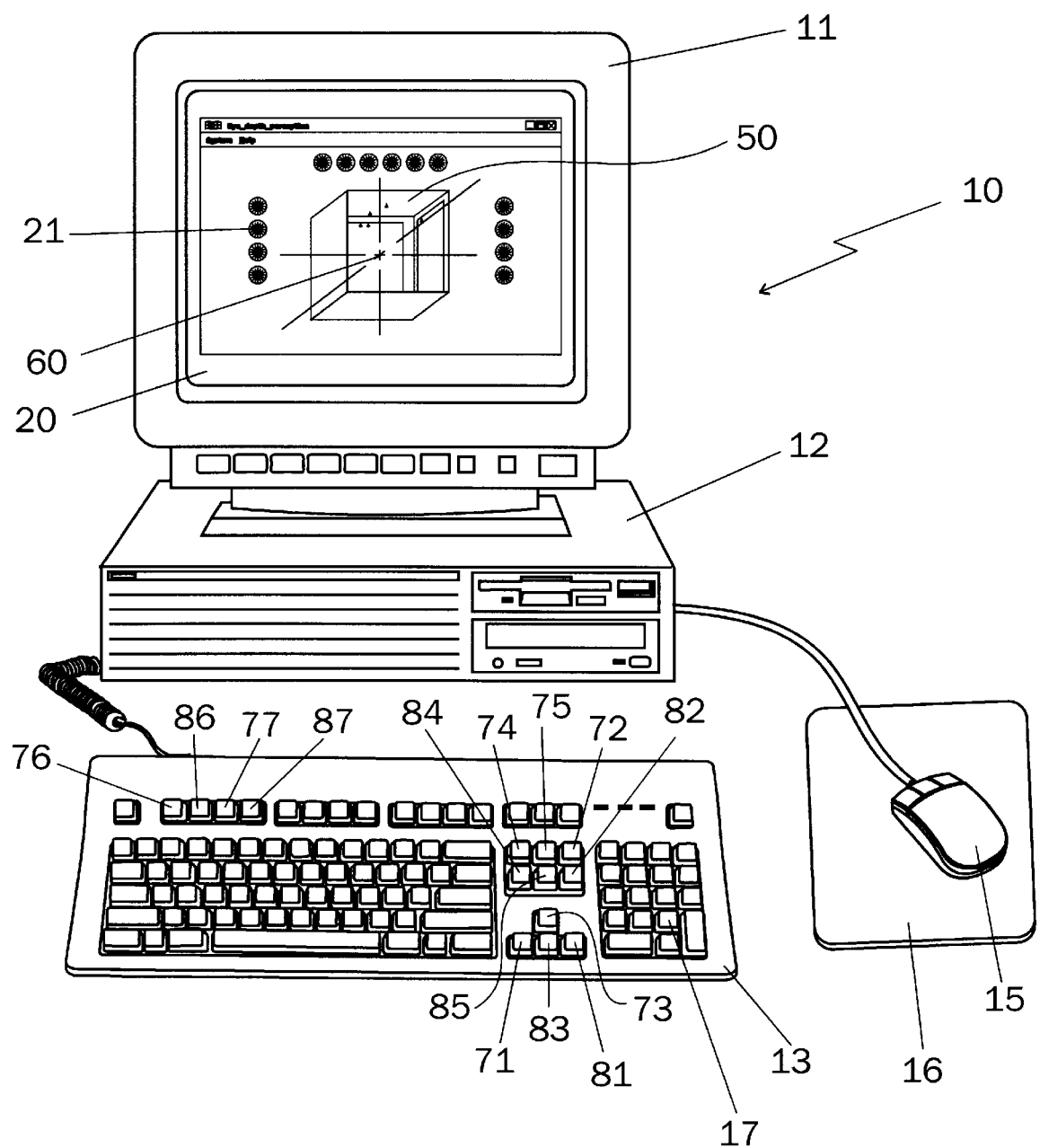
FIG. 1 is a perspective view of the apparatus used for eye depth perception testing according to the teachings of this invention.
Figure 2:
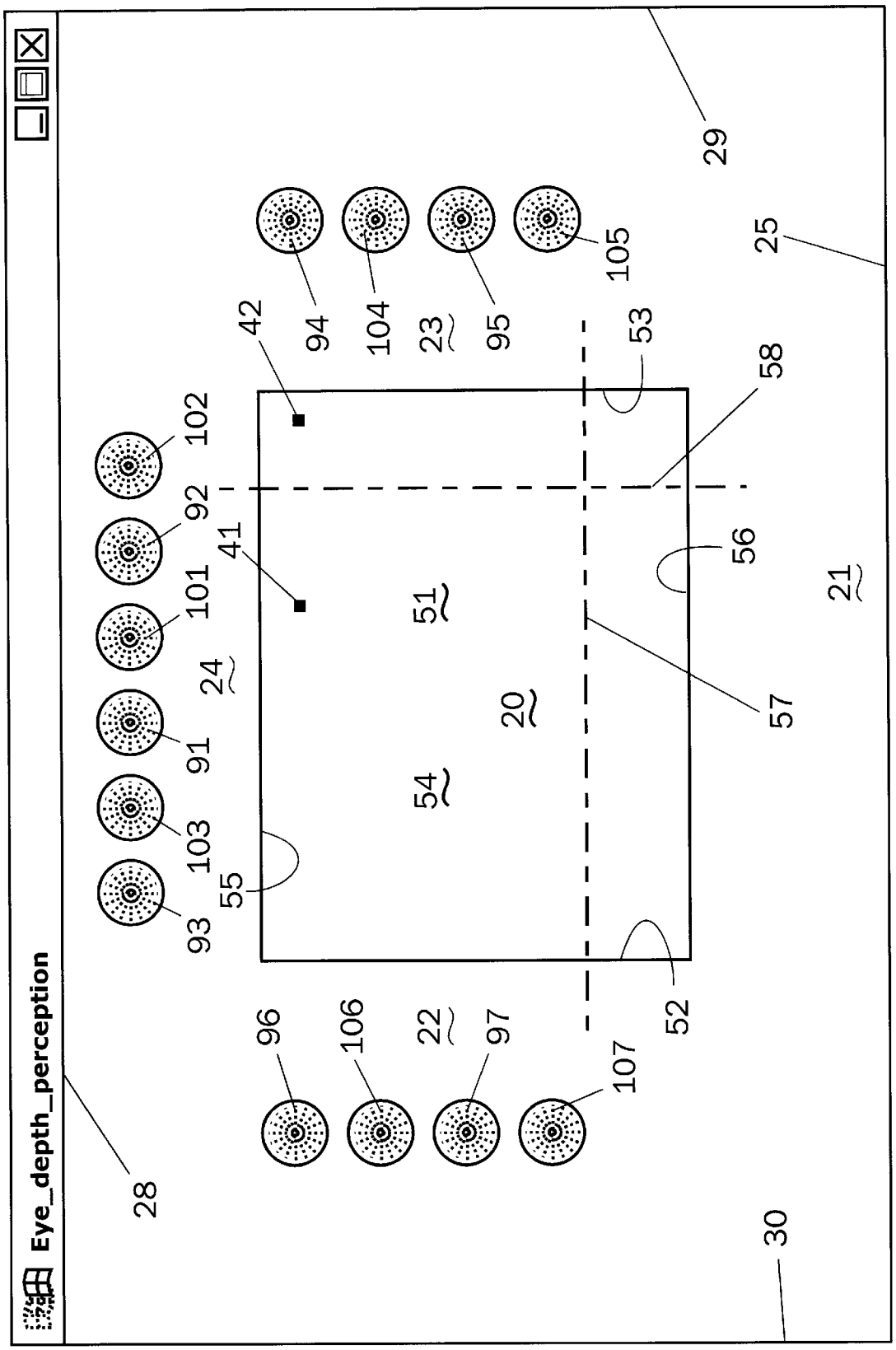
FIG. 2 is an enlarged plan view of display screen of the monitor of the apparatus of FIG. 1 showing a frontal plan view of the cubic space thereon having two images shown randomly spaced within the cubic space.
Figure 6:
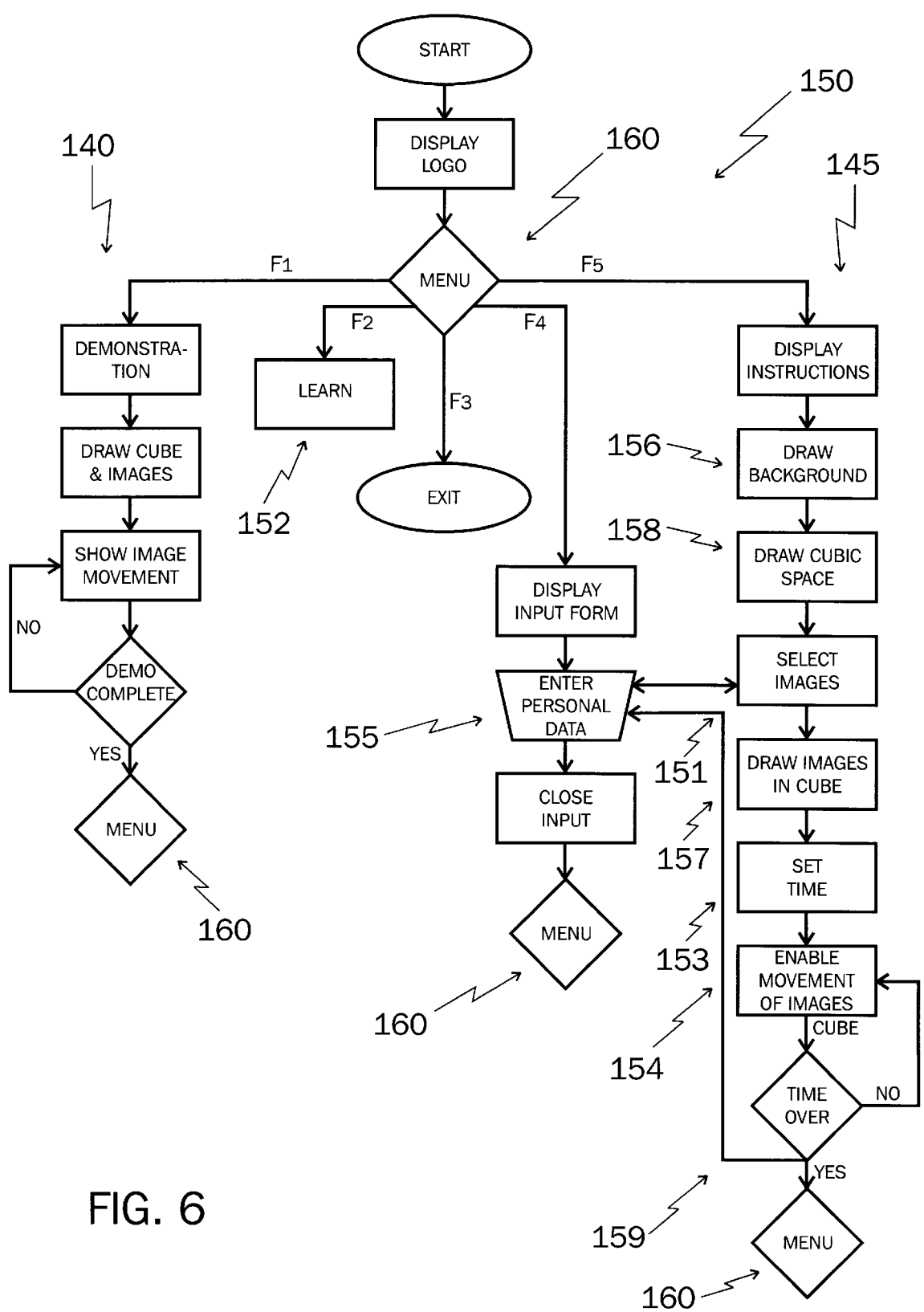
FIG. 6 is flowchart diagram of the program utilized in the apparatus of FIG. 1.

Referring now to FIG. 1, an electronic eye depth testing apparatus generally referred to by the numeral 10 comprises a central processing unit 12, a computer monitor 11 having a display screen 20, an eye depth testing program 150 of FIG. 6, a mouse 15 and a keyboard 13, central processing unit 12 having eye depth testing program 150 resident therein. Eye depth testing program 150 displays a three-dimensional cubic space generally referred to by the numeral 50 on display screen 20, eye depth testing program 150 displaying a first image 41 of a three dimensional object and a second image 42 of a three dimensional object in cubic space 50 on display screen 20. First and second images 41, 42, best seen in FIG. 2, are randomly placed in cubic space 50 wherein a subject to be tested moves images 41, 42 into convergence in the center 60 of cubic space 50. Hereinafter, walls 51–56 shall be interpreted to mean the interior surfaces of cubic space 50 as images 41, 42 are contained within the interior cubic volume of cubic space 50.

Keyboard 13 may be any keyboard which interfaces with central processing unit 12 wherein keyboard 13 has at least up and down arrow keys 73, 83 respectively, left and right arrow keys 71, 81 respectively, page up and page down keys 72, 82 respectively, insert and delete keys 74, 84 respectively, home and end keys 75, 85 respectively and function keys F1, F2, F3 and F4 keys 76, 86, 77, and 87 respectively or other keys which perform these same functions within central processing unit 12. Keys 71–75 and 81–85 are utilized to move images 41, 42 in cubic space 50 while the function keys 76, 86, 77, and 87 are used to rotate cubic space 50 as will hereinafter be fully described. For keyboards 13 having a numeric keypad 17, the number keys and the period key may be used for keys 71–75 and 81–85. Though keyboard 13 is one interface with central processing unit 12 and eye depth testing program 150 resident therein, eye depth testing program 150 further displays mouse interface buttons on a screen background 21 which may be energized with the click of a mouse button on mouse 15. The mouse interface buttons 91–97 and 101–107 perform the same functions as keys 71–75, 81–85 and function keys 76, 77, 86, 87 as will be hereinafter fully explained.

Referring now to FIGS. 2–5, display screen 20 on monitor 11 has screen background 21 surrounding cubic space 50 along the edges of display screen 20, three of these borders 22–24 have mouse interface buttons 91–97, 101–107 thereon arranged in rows parallel to the edges of display screen 20. Mouse interface buttons 91–97, 101–107 are shown as circular images however any shape of button could advantageously be utilized. Border 22 on the left side of cubic space 50 has cubic space rotation buttons 96, 106 and 97, 107 thereon. Border 23 on the right side of cubic space 50 has single image control buttons 94, 104, 95, and 105 thereon while top border 24 has simultaneous image control buttons 91–93 and 101–103 thereon, buttons 91–93 and 101–103 spaced below a program bar 26 and a command bar 27, wherein the program bar 26 and command bar 27 when used are arranged at the very top edge 28 of display screen 20. Cubic space 50 is shown in FIG. 2 as only one square face as cubic space 50 is arranged in orthogonal alignment with display screen 20 such that only open front wall 51 with a rear wall 54 directly in line therewith is viewable however, utilizing either function keys 77 and 87 or on screen mouse interface buttons 97 and 107, cubic space 50 may be rotated to the right or left, the left rotation shown in FIG. 3 so that right side wall 53 and rear wall 54 are viewable through open front wall 51. Similarly, function keys 76, 86, 77 and 87 or on screen mouse interface buttons 96, 97, 106 and 107 may be used singly or together to rotate cubic space 50 vertically and/or horizontally such that top wall 55, rear wall 54, bottom wall 56 and side walls 52, 53 are made visible through open front wall 51 though, of course, all walls 51–56 will appears reduced in size when cubic space is rotated and the interior surface of all walls 51–56 may not be observed simultaneously.

Figure 3:
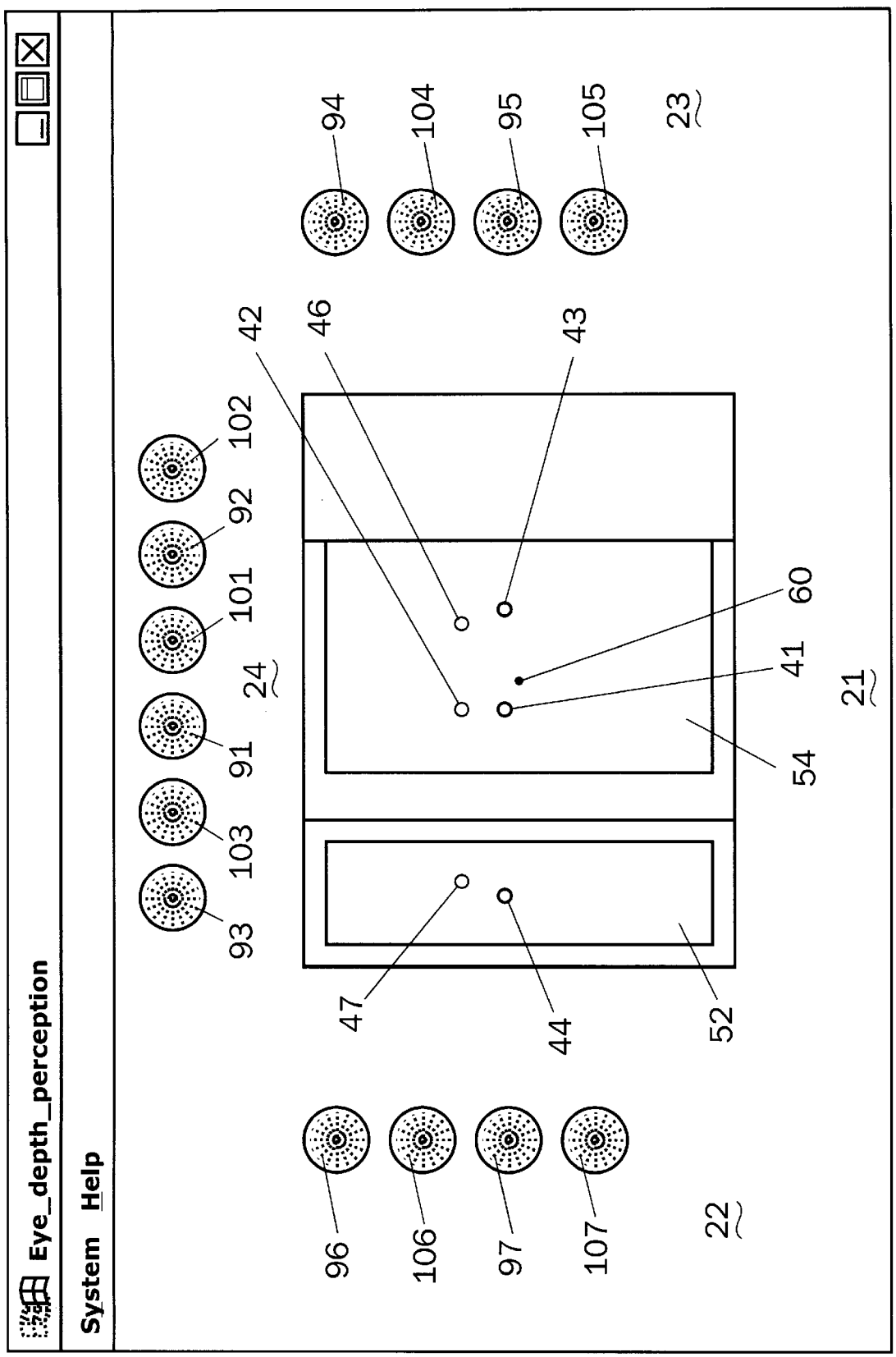
FIG. 3 is an enlarged plan view of display screen of the monitor of the apparatus of FIG. 1 showing the cubic space thereon having two images shown randomly spaced therein wherein the cubic space has been rotated to the left about a vertical axis and showing reflections of the two images on the left side wall and the rear wall.
Figure 4:
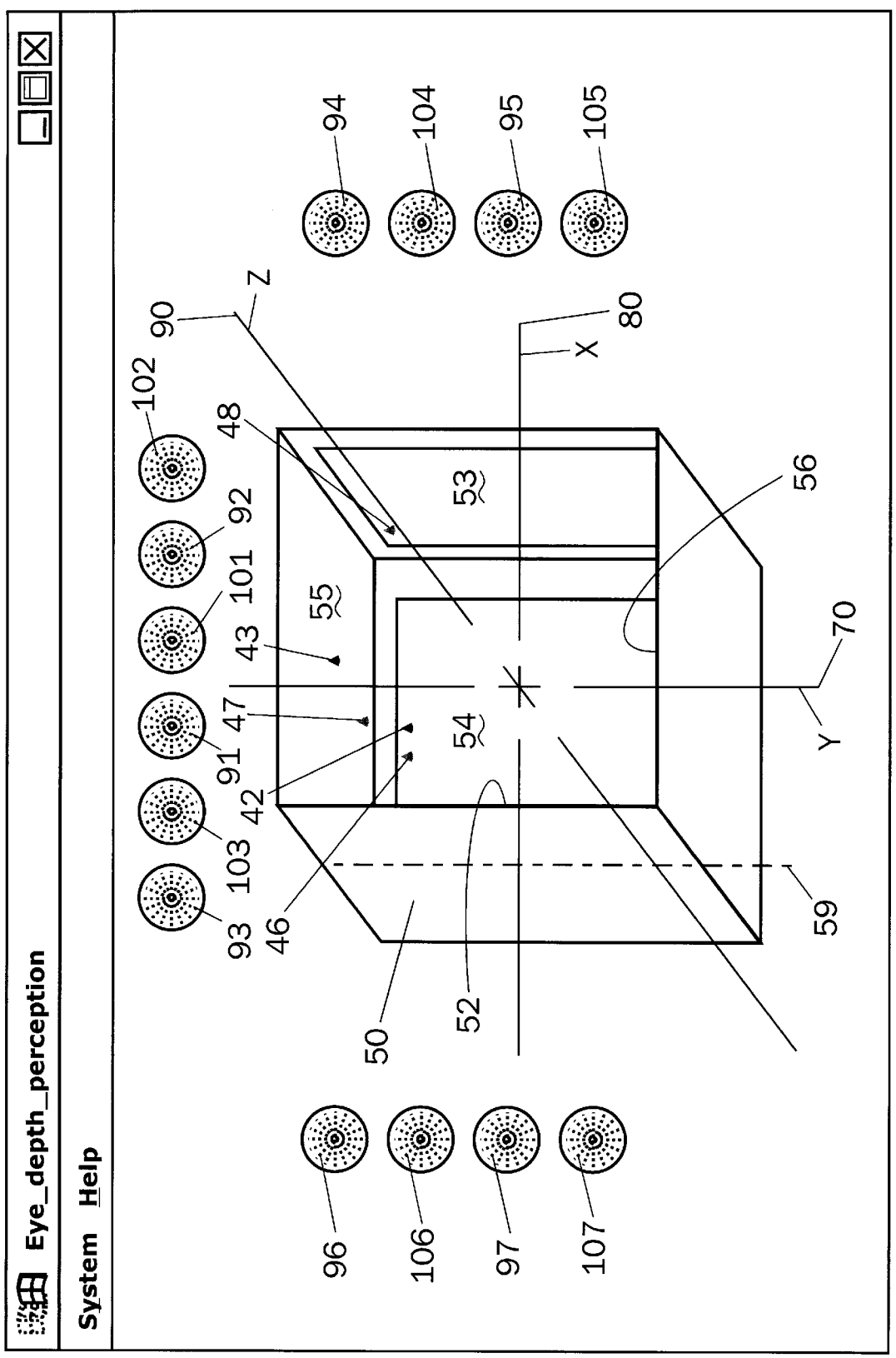
FIG. 4 is an enlarged plan view of the display screen of the monitor of the apparatus of FIG. 1 showing the cubic space thereon having two images shown randomly spaced therein wherein the cubic space has been rotated to the right about the vertical axis and upwardly about one horizontal axis showing reflections of the two images on the top wall and the rear wall.

As is readily apparent from viewing of FIG. 4, cubic space 50 comprises open front wall 51 and parallel rear wall 54, top wall 55, bottom wall 56 and side walls 52, 53, open front wall 51 and rear wall 54 each comprising a plane lying in the vertical direction parallel to the vertical axis 70 and the first horizontal axis 80, vertical axis 70 commonly referred to as the Y axis and first horizontal axis 80 commonly referred to as the X axis. Thus, open front wall 51 and rear wall 54 lie in the X-Y plane, are perpendicular to the Z axis and are spaced apart equidistant from and on an opposite sides of vertical axis 70 and first horizontal axis 80. Perpendicular to open front wall 51 and rear wall 54 are side walls 52 and 53, side walls 52, 53 lying a plane in a vertical direction parallel to vertical axis 70 and second horizontal axis 90, second horizontal axis 90 commonly referred to as the Z axis. Side walls 52 and 53 thus lie in the Y-Z plane, are perpendicular to the X axis and are spaced apart equidistant from and on opposite sides of vertical axis 70 and second horizontal axis 90. Completing cubic space 50, top wall 55 and bottom wall 56 are disposed in planes perpendicular to side walls 52, 53, open front wall 51 and rear wall 54 and lie in the X-Z plane spaced apart equidistant from and on opposite sides of first and second horizontal axes 80, 90 respectively. Hereinafter, vertical axis 70 and the term Y axis are synonymous. Likewise, first horizontal axis 80 and the term X axis are synonymous as are second horizontal axis 90 and the term Z axis. Though cubic space 50 is described above as a true parallelepiped having six perpendicular walls equally spaced from a central point, cubic space may be any other shape as desired wherein the shape has an aperture for viewing such as open front wall 51 of cubic space 50. Thus, an ellipsoid may be used wherein an aperture is provided on the surface of the ellipsoid with images 41, 42 disposed within the cubic space 50 defined by the interior of the ellipsoid. It is usually sufficient though, to conduct eye depth perception in a regular cubic space 50 as depicted in FIGS. 1–5.

As stated above, cubic space 50 is disposed into display screen 20 in FIG. 2 wherein only rear wall 54 is visible through open front wall 51. A series of first planes, such as horizontal plane 57, parallel to bottom edge 25 of display screen 20 and movable from bottom wall 56 to top wall 55 of cubic space 50 extend through side walls 52, 53, open front wall 51 and rear wall 54. A series of vertical planes, such as first vertical plane 58, parallel to right edge 29 and left edge 30 of display screen 20 and movable from right side wall 53 to left side wall 52 of cubic space 50 extend through top and bottom walls 55, 56, open front wall 51 and rear wall 54. Finally, a series of third planes (not shown) parallel to display screen 20 and movable from open front wall 51 to rear wall 54 of cubic space 50 extend through side walls 52, 53, top wall 55 and bottom wall 56. By referring to FIG. 4, it can be observed that series of horizontal planes 57 are perpendicular to the Y or vertical axis 70 and are movable therealong. Likewise, the series of first vertical planes 58 are perpendicular to the X axis 80 and movable therealong while series of second vertical planes 59 are perpendicular to and move along the Z axis 90. The series of planes described immediately above define various locations within cubic space 50, the number of planes 57, 58, 59 being infinitely variable in any of the three orthogonal directions between the walls 51–56 of cubic space 50. Images 41, 42 are randomly placed at the intersection of any three of the series of horizontal and first and second vertical planes 57, 58, 59 respectively, wherein images 41 and 42 may be coincident, though images 41 and 42 are usually placed at different intersections of different ones of the series of planes 57, 58, 59 within cubic space 50. Therefore, images 41, 42 may be placed at any location within cubic space 50. For instance, referring now to FIG. 2, first image 41 is located at the intersection of a horizontal plane parallel to horizontal plane 57, a vertical plane parallel to first vertical plane 58 and on a second vertical plane closer to open front wall 51 as first image 41 appears darker than second image 42. Second image 42 is located on the same horizontal plane as first image 41, however, second image 42 is disposed in a third vertical plane parallel to and spaced a different distance from first vertical plane 58, shown here as close to right side wall 53, and in a fourth vertical plane parallel with and spaced behind the second vertical plane wherein first image 41 resides as second image 42 is not as dark as first image 41. Thus, in FIG. 2, second image 42 is located nearer rear wall 54 while first image is located nearer open front wall 51.

Images 41 and 42 represent three dimensional objects and are selected from the group comprising cubes, pyramids, cones, dodecahedrons, ellipsoids, hyperboloids, cylinders parallelepipeds, spheres or any suitable three dimensional object. Preferably, cubes, pyramids and spheres are used and are randomly selected by eye depth testing program 150 for placement within cubic space 50. First image 41 and second image 42 are usually identical in shape but may be different in shape in order to test for shape related eye depth perception problems. First image 41 may also be larger or smaller than second image 42, however, generally images 41, 42 are of equal size. Likewise, images 41, 42 are usually of the same color however, each image 41, 42 may be a different color in order to determine eye depth perception problems related to color. Any of the myriad of colors of a color palette may be used for images 41, 42 however, it has been found by the teachings of this invention that the red, green and black colors are sufficient for eye depth perception testing. The illumination of cubic space 50 may be infinitely varied from dark to white light to test for eye depth perception problems at various lighting levels, however, lighting level in cubic space 50 is preferably limited to three levels, off, normal and bright. Finally, the location of the source of lighting may be varied throughout cubic space 50 however, six lighting sources have been found sufficient for the purposes set forth in this invention. Preferably, the lighting source is placed near the center of cubic space 50, or substantially at the center of open front wall 51, or substantially at the rear upper right corner or substantially at the lower rear corner of cubic space 50, or spaced inwardly toward center 60 from the upper front corner of cubic space 50 approximately two thirds the distance from center 60 or finally, spaced approximately inwardly toward center 60 from the upper front corner of cubic space one half the distance from center 60. Images 41, 42 are selected from among the various three dimensional objects, colors, sizes, location of light source and level of ambient light utilizing a random number generator which selects the images 41, 42 according to the algorithm used for the random number generator. Of all the possible combinations of the preferred three shapes, three colors, six locations and three levels of illumination only sixty are used, one for each second of chronological time in a given minute. It has been found by the teachings of this invention that these sixty combinations effectively eliminate a familiarity factor from eye depth testing, however, as any of these parameters may be changed by inserting the proper command in eye depth testing program 150, it is impossible for any given subject to be tested at identical conditions thereby totally eliminating a familiarity factor from the eye depth test.

Figure 5:
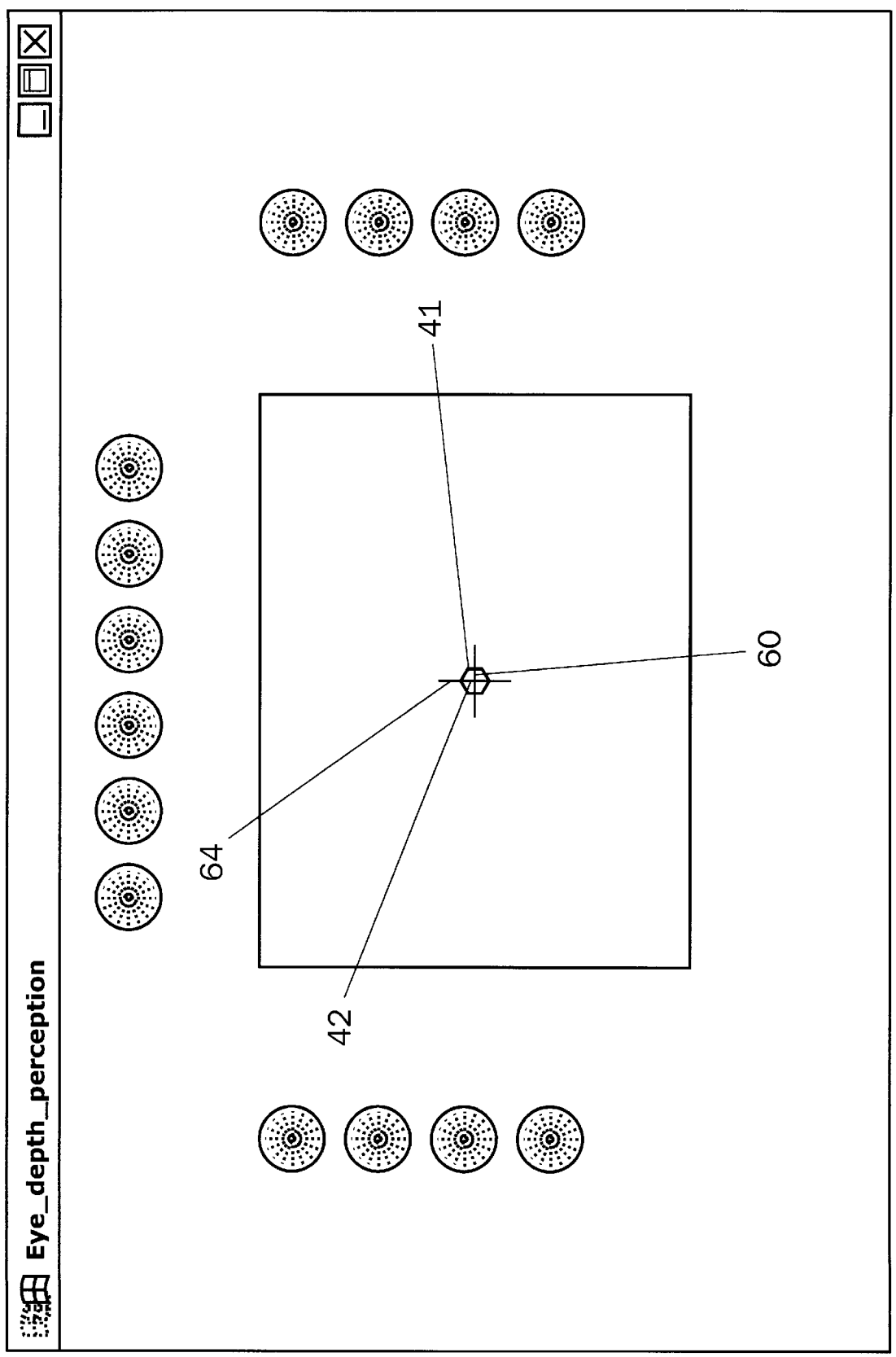
FIG. 5 is an enlarged plan view of display screen of the monitor of the apparatus of FIG. 1 showing the cubic space thereon having two images shown in convergence at a center of the cubic space.

Although the location of source lighting and the intensity thereof is varied by the random selection of the parameters of the test, some subjects may be incorrectly assessed as having eye depth perception difficulties from the shadows generated by the location and intensity of the light source. To eliminate all possibility of shadowing and to prevent light absorption by the walls of cubic space 50, at least one reflective surface on at least one horizontal wall and/or at least reflective surface on at least one vertical wall is provided. Mirroring of the walls carries forward to this invention this feature of the aforementioned U.S. Pat. No. 4,260,226 by the inventor of this invention, the specification of which is fully incorporated into this application by this reference thereto. Preferably, each of walls 52–56 are provided with a reflective surface covering the entirety of the interior surface of these respective walls such that cubic space 50 comprises an internally mirrored box with one open front wall 51. FIGS. 3 and 4 show walls 52, 53 and 54 as having a mirrored surface smaller than the entirety of the wall surface, however, this effect is shown only to draw attention to the reader of this specification that the respective wall has a mirrored surface, it being understood that the entirety of the surface of walls 52–56 is reflective. With the entirety of walls 52–56 made reflective, images 41, 42 may be observed in an actual position and/or in a primary reflected position on any of the reflective surfaces of walls 52–56. Though the entirety of each of interior walls 52–56 is reflective, walls 52–56 produce only a primary reflection of image 41, 42. No secondary image of a reflection occurs in order to eliminate confusion of which reflection is a true reflection and which reflection is a secondary image. Referring to FIG. 2, no reflected image is viewable as images 41, 42 cover the reflection from rear wall 54 since cubic space 50 in FIG. 2 is observed through open front wall 51 and images 41, 42 are in direct line with the respective reflection thereof while reflected images may be observed in FIGS. 3 and 4 as cubic space 50 is rotated such that images 41, 42 are not in direct line with the respective reflections thereof. For instance, in FIG. 3, first image 41 is shown as a spherical object near center 60 of cubic space 50 with a first reflection 43 shown on rear wall 54 aligned on the horizontal plane with first image 41. A second reflection 44 of first image 41 is shown on left side wall 52 also aligned on the same horizontal plane as first image 41 and first reflection 43. A subject to be tested may then infer from the reflections 43, 44 that first image 41 is to the left and forward of center 60 and substantially aligned with the X-Z plane and may make suitable adjustments using the keyboard keys or the mouse buttons alongside cubic space 50. Similarly, second image 42 is shown above first image 41 with one reflection 46 appearing on rear wall 54 and another reflection 47 appearing on left side wall 52 these reflections 46, 47 in the same plane as second image 42. The subject to be tested may infer from these reflections 46, 47 that second image 42 is to the left of, behind and above center 60. Second image 42 appears to be behind center 60 as second image 42 is lighter than first image 41, the different intensities of the images 41, 42 shown by a different line weights. Again, the subject to be tested may make the suitable adjustments to one or both images 41, 42 to bring these images 41, 42 into convergence at center 60 as shown in FIG. 5.

Referring now to FIG. 4, first image 41 is hidden by the rotation of cubic space 50 in the upward right direction as first image 41 is near bottom wall 56 as only the first reflection 43 of first image 41 is observable in the reflective surface of top wall 55. Hence, first image 41 must be moved upwardly along the vertical plane toward center 60 in order to see other reflections in right side wall 53 and rear wall 54. Second image 42 however, is viewed as being near rear wall 54 as one reflection 46 is observed close to and to the left of second image 42 in rear wall 54 with another reflection 47 observed close to and above second image 42 in top wall 55. A third reflection 48 of second image 42 is observed in right side wall 53 near the intersection of the three walls at the upper right rear corner. As first image 41 appears to be approximately the same distance to the right of vertical Y axis 70 as second image 42 is to the left thereof and first image 41 is as near the bottom wall 56 as second image 42 is near to the top wall 55, the subject to be tested may move both images 41, 42 simultaneously toward center 60 to bring both into a better viewing for further movement toward convergence as shown in FIG. 5.

Electronic eye depth testing apparatus 10 comprises a three dimensional cubic space 50 displayed on a display screen 20, cubic space 50 having a first image 41 of a three dimensional object and a second image 42 of a three dimensional object randomly placed within cubic space 50. First image 41 is located at the intersection of two perpendicular vertical planes 58, 59 and horizontal plane 57 perpendicular to vertical planes 58, 59 and second image 42 is located at the intersection of two perpendicular vertical planes 58, 59 and horizontal plane 57 perpendicular to vertical planes 58, 59, wherein a subject to be tested moves images 41, 42 into convergence in the center 60 of cubic space 50 by moving images 41, 42 equally and in opposite directions in at least one of a series of horizontal parallel planes 57 using one pair of keys 71, 81 on a keyboard device 13 used for controlling images 41, 42 on display screen 20, equally and in opposite directions in one of series of first vertical parallel planes 58 using a second pair of keys 72, 82 or equally and in opposite directions in at least one of a series of vertically disposed third parallel planes using a third pair of keys 73, 83. For instance, referring to FIG. 2, first image 41 and second image 42 may be moved toward or away from each other in horizontal plane 57 in which they reside by depressing the left arrow key 71 or right arrow key 81. Experimentation will determine which key to depress, however preferably the arrow keys 71, 73, 81 and 83 refer to movement of first image 41 in the direction indicated. Therefore, referring again to FIG. 2, a subject to be tested moves images 41 and 42 closer together along the X-Z plane in which images 41, 42 reside by depressing right arrow key 81 which simultaneously moves first image 41 to the right and second image 42 to the left. First image 41 may be moved to the right of second image 42 by holding down right arrow key 81 until first image 41 passes second image 42 though this movement is not desirable in the instant case. Likewise, first image 41 may be moved upwardly or downwardly by depressing either up arrow key 73 or down arrow key 83 with second image 42 moving in a direction opposite the movement of first image 41. For instance, if down arrow key 83 is depressed, second image 42 will move upwardly and first image 41 will move downwardly along the Y-Z plane in which images 41, 42 reside until second image 42 is in contact with top wall 55 wherein movement of both images 41, 42 will cease. It is readily apparent that in order to move images 41, 42 into convergence at center 60, movement of images 41, 42 simultaneously in opposite directions upwardly and downwardly respectively is not in the best interest of the subject for this example at this time. It may be advantageous for the subject in the example shown in FIG. 2 to align images 41 and 42 within the same vertical plane parallel to open front wall 51 of cubic space 50 before attempting any other moves as first image 41 appears to be closer to open front wall 51 than second image 42. Therefore, images 41 and 42 may be moved in the horizontal plane into and out of cubic space 50 by using page up key 72 and page down key 82 until images 41, 42 appear to be the same size and brightness. Page up is defined as plus on the Z axis therefore, page up key 72 will move first image 41 forward along the X-Y plane in which images 41, 42 reside toward open front wall 51 while second image 42 moves toward rear wall 54. In FIG. 2, it is apparent that using page up key 72 will put further distance between images 41, 42 therefore it is advantageous to use page down key 82 to move first image 41 toward rear wall 54 while moving second image 42 toward open front wall 51 until first image 41 and second image 42 appear to be equal in brightness indicating that images 41, 42 are approximately in the same vertical plane passing through the side walls 52, 53, top wall 55 and bottom wall 56. Though this move may align images 41, 42 in the same vertical plane recited above, other movements are necessary to bring images 41, 42 into convergence at center 60.

Thus, in order to bring images 41, 42 into convergence at center 60, it is necessary to move one image 41 or 42 while the other image 42 or 41 remains stationary. Therefore, a fourth pair of keys 74, 84 are provided to move one of images 41, 42 along the X-Z horizontal plane in which image 41, 42 resides depending upon the location of images 41, 42. Eye depth testing program 150 will allow for movement of only one of images 41, 42 as it is immaterial which individual image 41, 42 is moved utilizing fourth pair of keys 74, 84. For instance, in FIG. 2, it is readily apparent that one of images 41, 42 must be moved to a location on the left side of the Y axis a distance substantially equal to the distance the image remaining stationary lies to the right side of the Y axis. Therefore, if eye depth testing program 150 designates first image 41 to be moved, the selection of which is evident by depressing one of keys 74, 84, first image 41 would be moved to the left of the Y axis. As delete key 84 is defined as movement in the left direction, it is apparent to the subject being tested that only delete key 84 need be depressed to move first image 41 to a location to the left of the Y axis an amount substantially equal to the distance second image 42 remains to the right of the Y axis and therefore, first image 41 must be moved substantially to left side wall 52 by depressing delete key 84 thus putting images 41, 42 equally spaced from the Y axis and on opposite sides thereof such that first pair of keys 71, 81 may then be utilized to move images 41, 42 together toward the Y axis and hence in substantial alignment therewith thereby completing one of the necessary orthogonal moves to place images 41, 42 at center 60 of cubic space 50. Keys 72, 82 may then be utilized to move both images 41, 42 upwardly and downwardly in equal and opposite directions, however as images 41, 42 are both near top wall 55, it will be most advantageous to the subject being tested to put images 41, 42 on opposite sides of the X axis substantially at bottom wall 56 by moving one image 41 or 42 while the other image 42, 41 remains stationary. Thus, fifth pair of keys 75, 85 are utilized. As key 75 is defined as up, it is apparent that end key 85 is desired as it is again immaterial which image 41, 42 is moved. Depressing end key 85 will then allow movement of one of images 41, 42 to a location near bottom wall 56 such that images 41, 42 are on opposite sides of the X axis and spaced substantially equally therefrom. Keys 72, 82 may then be used to bring images 41, 42 in substantial alignment with the X axis. Images 41, 42 may now appear to be aligned at center 60 of cubic space 50, however, alignment has only been completed with the X and Y axes and first image 41 could be spaced forward of second image 42 although it is not readily apparent as first image 41 lies over second image 42 and second image 42 is no longer visible. Thus, rotation of cubic space 50 is required to determine the spatial alignment of first image 41 with respect to second image 42 along the Z axis and bring first image 41 into alignment with second image 42 at center 60.

Cubic space 50 may be rotated right or left by depressing the F3 or F4 keys respectively. Rotation of cubic space 50 will show that second image 42 is behind center 60 and first image 41 is spaced in front of center 60 an equal amount and hence it is only necessary to move images 41, 42 together along the Z axis to bring images 41, 42 into substantial alignment with center 60. Movement of images 41, 42 along the Z axis was only necessary as eye depth testing program 150 usually places images 41, 42 in equal and opposite directions from the X-Y plane although an alternative embodiment below allows for alignment of images 41, 42 at center 60 even if images 41, 42 are not equally spaced from center 60 in at least one direction and hence images 41, 42 could be moved into alignment with center 60 where both images 41, 42 were in the same location within cubic space 50 at the beginning of an eye depth test using eye depth testing program 150 as will be hereinafter fully explained.

Eye depth perception program 150 provides for alternate movement of images 41, 42 by clicking on one of a series of on-screen buttons. For instance, in FIG. 2, movement of first image 41 to the right while second image 42 remains stationary is accomplished by using mouse 15 to place the cursor on the top right side button 94 and repeatedly clicking top right button 94 until first image 41 moves to the desired location. As in the discussion above, it is more advantageous to move first image 41 to the left and therefore, the cursor should be placed on the second right side button 104 and repeatedly clicking until first image 41 is moved near left side wall 52. Still referring to FIG. 2, movement of first image 41 upward and downward is accomplished by clicking on third right side button 95 and bottom right side button 105 respectively. Once first image 41 is moved to a location near left side wall 52, first image 41 may be moved to a location near bottom wall 56 by repeatedly clicking on bottom right side button 105 to move first image 41 downwardly along left side wall 52 while second image 42 remains fixed near the intersection of top wall 55 and right side wall 53. Of course, if first image 41 would need to be moved upwardly, third right side button 95 would be clicked repeatedly until first image 41 would be moved to the desired location.

Once the movements recited above utilizing second and bottom right side buttons 104, 105 respectively, simultaneous movement of images 41, 42 is desired to move images 41, 42 toward center 60. Thus, it is necessary to utilize the upper buttons 91–93 and 101–103. Left upper button 93 will move images 41, 42 simultaneously vertically together while second upper button 103 moves images 41, 42 simultaneously vertically apart. Since first image 41 has been moved to a location near the intersection of left side wall 52 and bottom wall 56 while second image has remained near the intersection of right side wall 53 and top wall 55, left upper button 93 must be repeatedly clicked to move images 41, 42 vertically toward each other. The subject to be tested can move images 41, 42 along left side wall 52 and right side wall 53 respectively until images 41, 42 appear to be in substantial horizontal alignment whereupon movement of images 41, 42 horizontally together toward center 60 must be attempted. Movement of images 41, 42 simultaneously together horizontally is accomplished by repeatedly clicking on fourth upper button 101 as fourth upper button 101 has been defined for simultaneous movement of first image 41 toward second image 42 while third upper button 91 has been defined for simultaneous movement of first image 41 away from second image 42. Continuing the example begun above, the subject moves images 41, 42 together horizontally until first image 41 appears to cover second image 42. In case, vertical alignment was not fully accomplished by utilizing right side buttons 95 or 105, movement image 41 can then be attempted by re-selection of the proper button 95, 105. Similarly, if horizontal alignment was not fully accomplished, a second movement of first image 41 is attempted by utilizing right side buttons 94 or 104. Finally, if vertical alignment of images 41, 42 at the X-Z plane through center 60 was incomplete, movement of images 41, 42 simultaneously is again accomplished by utilizing first and second upper buttons 93, 103.

Though alignment in the horizontal and vertical directions in the plane of open front wall 51 may have been completed in the example recited above, alignment along the Z axis may yet be incomplete as images 41, 42 may have been randomly placed on opposite sides of the X-Y plane. Therefore, cubic space 50 must be rotated either right, left, and/or up or down to view first image 41 with respect to second image 42 along the Z-axis. Rotation of cubic space 50 is accomplished with on-screen buttons 96, 97, 106, 107. For instance, to rotate cubic space 50 as shown in FIG. 2 to the left to produce the presentation of cubic space 50 as shown in FIG. 3, bottom left side button 107 performs the same function as F4 key 87 and repeated clicking upon bottom left side button 107 rotates cubic space 50 to the left through incremental movements. Therefore, first image 41 will most likely appear to be disposed forward of center 60, that is to the left in FIG. 3, while second image 42 will most likely appear to be disposed behind center 60. The subject to be tested then utilizes fifth upper button 92 to move first image 41 toward second image 42 as fifth upper button 92 has been defined for movement of images 41, 42 toward each other when image 41 is disposed forward of image 42. Of course, if second image 42 is disposed forward of first image 41, right upper button 102 is utilized to move images 41, 42 together as right upper button 102 has been defined for movement of images 41, 42 toward each other when image 42 is disposed forward of image 41. Rotation of cubic space 50 to the representation shown in FIG. 3 has been described as rotated toward the left from the representation shown in FIG. 2 using bottom left side button 107, however third left side button 97 may be used to rotate cubic space toward the right which would produce a representation substantially opposite that shown in FIG. 3. Similarly, top left side button 96 may be used to rotate cubic space 50 upwardly while second left side button 106 may be used to rotate cubic space 50 downwardly.

Referring now to FIG. 4, it is apparent that cubic space 50 has been rotated to the right but repeatedly clicking upon third left side button 97 and further rotated upwardly by repeatedly clicking upon second left side button 106 such that at least a portion of three of the interior walls, 53, 54 and 55 are visible through open front wall 51. Those skilled in the art will appreciate that rotation of cubic space 50 downwardly and to the left may be accomplished by using top left side button 96 for rotation to downwardly and bottom left side button 107 for rotation to the left.

Some subjects to be tested may prefer rotation of cubic space 50 into the three dimensional representation shown in FIG. 4 before attempting to move images 41, 42 thus allowing the subject to be tested to observe second image 42 and reflections 46, 47 and 48 thereof and reflection 43 of first image 42. As first image 41 is near bottom wall 56 and is hidden by the rotation of cubic space 50 in the upward right direction, therefore only the first reflection 43 of first image 41 is observable in the reflective surface of top wall 55. Hence, first image 41 must be moved upwardly along the vertical plane toward center 60 using third right side button 95 in order to see other reflections of first image 41 in right side wall 53 and rear wall 54. Second image 42 however, is viewed as being near rear wall 54 as one reflection 46 is observed close to and to the left of second image 42 in rear wall 54 with another reflection 47 observed close to and above second image 42 in top wall 55. A third reflection 48 of second image 42 is observed in right side wall 53 near the intersection of three walls 53, 54 and 55 at the upper right rear corner. As first image 41 appears to be approximately the same distance to the right of vertical Y axis 70 as second image 42 is to the left thereof and first image 41 is as near the bottom wall 56 as second image 42 is near to the top wall 55, the subject to be tested may move both images 41, 42 simultaneously vertically toward the X-Z plane and hence center 60 using left upper button 93 to bring first image 41 into a better viewing for further movement toward convergence as shown in FIG. 5. Thereafter, fifth upper button 92 may be used to move images 41, 42 in the Z direction toward the X-Y plane as it is apparent that first image 41 is forward of the X-Y plane while second image 42 is therebehind. Finally, third upper button 91 may be used to move first image 41 to the left while second image 42 moves simultaneously to the right as reflection 43 of first image 41 appears to be approximately the same distance to the right of the Y-Z plane as first reflection 47 of second image 42 is displaced to the left of the Y-Z plane. When images 41, 42 appear to be disposed an equal distance from and on opposite sides of each of the three axes 70, 80, 90, rotation of cubic space 50 as shown in FIG. 4 becomes quite beneficial to the subject to be tested.

Though movement of images 41, 42 has been described by utilizing keys 71–77 and 81–87 on keyboard 13 or by on-screen buttons 91–97 and 101–107, it is entirely possible to utilize both keys 71–77, 81–87 and on-screen buttons 91–97, 101–107 together to bring images 41, 42 into convergence at center 60. For instance, the user may move first image 41 singly to the left utilizing keyboard key 84 while simultaneously moving first image 41 downwardly toward bottom 56 by repeatedly clicking on third right side button 105 using mouse 15 thereby achieving the same results as described in the example above using these functions separately. Similarly, the user may click repeatedly on second left side button 106 to rotate cubic space 50 upwardly while simultaneously repeatedly depressing function key F3 to rotate cubic space 50 to the right to place cubic space 50 into the position shown in FIG. 4. Of course, simultaneous use of other on-screen buttons and other keyboard keys is also possible provided that a key selected from keys 71–77, 81–87 and a button selected from on-board screen buttons 91–97, 101–107 are not programmed for the same type of movement as no simultaneous result would then occur.

A flow chart for eye depth perception program 150 is shown in FIG. 6 wherein eye depth perception program 150 comprises four different modules selectable from a menu screen 160. Program 150 was developed in VC++ utilizing Microsoft® Access '2000 for use in Windows® 95, Windows® 98, Windows NT® on a personal computer having a system processing speed of 200 MHz though any program language may be used. Furthermore, a processor having a greater or lesser speed may be utilized without departing from the scope of this invention. Program 150 is available on CD-ROM or floppy discs and a demonstration may be observed on the Internet. Eye depth perception testing described above is available by selecting function key F5 at the menu screen wherein the subject to be tested is first given instructions before eye depth perception testing is begun, however at least one other selection from menu 160 is required and at least one other selection from menu 160 is suggested before beginning testing. For instance, by selecting function key F1, a subject to be tested may observe a demonstration, represented by numeral 140, of the system wherein cubic space 50 is first drawn with images 41, 42 randomly placed within cubic space 50, cubic space 50 shown in one of two different configurations, planar as in FIG. 3 and three dimensional as in FIG. 4. Demonstration 140 then proceeds to show individual movement or simultaneous movement of images 41, 42 and rotation of cubic space 50. Images 41, 42 are moved in a manner similar to the manner to be utilized in actual eye depth testing such that images 41, 42 proceed toward center 60 of cubic space 50. In demonstration 140, center 60 appears as a small colored dot centered on cross hairs 64 and represented in FIG. 5 as a hexagon. Center 60 only appears in demonstration 140 and in learning step 152 and thus the subject to be tested must rely upon spatial perception in order to visualize a virtual center 60 during eye depth perception testing. Demonstration 140 proceeds over an allotted demonstration time of about two minutes through several iterations of the movement of images 41, 42 until images 41, 42 are moved into convergence with center 60 as shown in FIG. 5. When demonstration 140 is complete, demonstration 140 returns the subject to be tested to menu 160 for another selection. Of course, demonstration 140 may be repeated however, a subject to be tested is usually ready for either testing step 145 or learning step 152 after one demonstration 140.

Preferably, a subject to be tested first selects function key F4 and completes the necessary information in personal data step 155 by entering personal data in an input form. The personal data form includes vital statistical information about the subject to be tested and therefore includes name, age, gender, eye correction, eyewear, color blindness and physical activity just prior to the test, all this statistical information keyed to a specific personal identification number provided by an administrator of the eye depth testing system 10. Thus, a subject to be tested may be tested on more than one occasion by entering their specific personal identification number at the beginning of each test subsequent to the first test. In addition to the known physical factors, physical exertion prior to eye depth testing has been found to significantly affect eye depth perception depending upon the amount of physical exertion prior to the test, hence it is important to record physical activity in the time frame just prior to eye depth testing. Personal data gathered in personal data step 155 is used to generate statistical information about eye depth perception of a class of subjects for use in government, military, academic and industrial institutions by keying the results of testing step 145 to the personal data represented by each personal identification number. The statistical data may be analyzed in a manner similar to that employed in a doctoral dissertation presented in February 1984 to the Graduate Faculty of Louisiana Technical University by the inventor of this invention, this doctoral dissertation incorporated into this disclosure by this reference hereto. Though the personal identification number is preferably given by an administrator of the test, eye depth testing program 150 may automatically assign a number to each user whereby multiple tests by a single user would be keyed together utilizing the totality of the information entered at personal data step 155. At the completion of personal data step 155, the subject to be tested is returned to menu 160 for selection of another step in eye depth perception testing program 150.

For instance, the subject to be tested may select either learning step 152 or testing step 145. Learning step 152 and testing step 145 are identical in operation except center 60 is virtual in testing step 145 while center 60 is actual as described above in demonstration step 140 and testing step 145 has a specified time limit before testing step 145 closes and returns the user to menu 160. Therefore, the flow chart symbols for learning step 152 are omitted and the operation of testing step 145 will now be described in detail. In testing step 145, instructions are first displayed to alert the subject to be tested to the object of the test and which keys are used for movement of images 41, 42 and for rotation of cubic space 50. Further instructions alert the user to the proper operation of on-screen buttons 91–97 and 101–107. Finally, the instructions inform the user about the time limit for eye depth perception testing. After reading and understanding the instructions, the user presses the enter key and testing step 145 enters an automatic mode wherein cubic space 50 is first drawn in orthogonal alignment with display screen 20 such that only rear wall 54 is visible behind open front wall 51. Testing step 145 then proceeds to select the size, shape and color of images 41, 42 and the location and intensity of a light source lighting cubic space 50 in image selection step 151. Selection of images 41, 42 in image selection step 151 is keyed to personal data step 155 to ensure that a subject to be tested does not repeat any test previously taken in order to completely eliminate the possibility of a familiarity factor with eye depth testing program 150. Therefore, though there are sixty possible combinations of image size, shape, color, level of lighting intensity and location of lighting source, a subject to be tested repeating eye depth testing will not be given a familiar placement, size, color or size of images 41, 42 as previously run tests for a particular subject to be tested are recorded in personal data step 155. Preferably, selection of images 41, 42 is keyed to a random number generator which selects images 41, 42 in image selection step 151 from the myriad of possible selections based upon the time which the subject begins entering data into personal data step 155. In image placement step 157, placement of images 41, 42 into cubic space 50 is also accomplished by a random number algorithm such that placement of images 41, 42 in the same location follows no specific pattern to again remove any familiarity factor from testing step 145. Once testing step 145 has selected images 41, 42 in image selection step 151 and placed images 41, 42 in cubic space 50 in image placement step 157, a time clock in set time step 153 begins a countdown from the preselected time frame which has been found by the teachings of this invention to be about three hundred seconds utilizing the 200 MHz processor. Thus, the preferred set time is three hundred seconds and an on-screen clock displays the remaining time upon every key stroke or every click of the mouse button on mouse 15. The user then moves images 41, 42 individually or simultaneously in movement step 154 as set forth above to accomplish the object of aligning images 41, 42 at orthogonal coordinates 0, 0, 0 for each of images 41, 42 at center 60 within the allotted time established in set time step 153. Decision step 159 determines the expiration of the allotted time and at the expiration of the allotted time closes the window and stores the final three dimensional orthogonal position of each image 41, 42 in a database keyed to the personal identification of the subject being tested. At the conclusion of testing step 145, the administrator can determine the orthogonal position of images 41, 42 by utilizing the system command on program bar 26 and the appropriate password, however, the user is prevented from doing so. The user may obtain help by clicking on the help command on program bar 26 for a description of the function of all the keys and answers to frequently asked questions. In learning step 152, the user may determine the orthogonal coordinates of images 41, 42 at any time by pressing the F7 key for spherical and cubic images 41, 42 and function key F8 for pyramidal and other polygonal images 41, 42. The user cannot stop testing step 145 before expiration of the three hundred seconds set time as the window closes only at the expiration of the set time returning the user to menu 160. A user may repeat testing step 145 in order to establish another data point in the statistical database. Preferably, multiple subjects are tested thereby continually adding to the statistical database. Though the time to required by a subject to be tested to center images 41, 42 is not recorded in the database, where program 150 is utilized on a computer having a greater processing speed, program 150 may automatically change the allotted time for completion of testing step 145 or program 150 may have the allotted time for completion changed by the system administrator.

In an alternative embodiment, control of images 41, 42 may be accomplished by using the shift, alternate and control keys along with the arrow keys to allow for movement of both images 41, 42 in the orthogonal directions each of shift, alternate and control being used for movement within a particular plane. For instance, use of the four arrow keys alone is defined for movement of images 41, 42 simultaneously in the X-Y plane while the use of shift with the four arrow keys is defined for movement of images 41, 42 simultaneously in the X-Z plane and alternate with the four arrow keys allows movement of images 41, 42 in the Y-Z plane. Movement of cubic space 50 may be accomplished by utilizing control with the four arrow keys such that cubic space 50 may be rotated right or left, up or down by holding down the control key while depressing the appropriate arrow key. In this alternate embodiment, insert key 74 may be used to move first image 41 in the positive X direction with image 42 remaining stationary while delete key 84 would be used to move first image 41 in the negative X direction. Home key 75 is defined as movement of only first image 41 in the positive Y direction while end key 85 is defined for movement of only first image 41 in the negative Y direction. Finally, page up key 72 allows for single movement of image 41 in the positive Z direction while page down key 82 moves first image 41 in the negative Z direction.

In yet other alternate embodiments of this invention, movement of cubic space 50 and images 41, 42 may be accomplished by the use of at least one joy stick, eye movement detection devices of the art field such as cited above or speech recognition software now available on the market by utilizing program 150 to control images 41, 42 and/or cubic space 50 in the requisite orthogonal directions in testing step 145 or learning step 152 based on inputs from these alternate devices. Furthermore, main menu step 160, personal data step 155 and demonstration step 140 may also be accessed by these alternate devices. Thus, eye depth perception system 10 is accessible to persons having disabilities.

While the present invention has been described with reference to the above described preferred embodiments and alternate embodiments, it should be noted that various other embodiments and modifications may be made without departing from the spirit of the invention. Therefore, the embodiments described herein and the drawings appended hereto are merely illustrative of the features of the invention and should not be construed to be the only variants thereof nor limited thereto.

I claim:

1. An electronic eye depth testing method comprising a three dimensional cubic space displayed on a display screen, said cubic space having a first image of a three dimensional object and a second image of a three dimensional object, said first and said second images randomly placed within said cubic space, said first image located at the intersection of two perpendicular vertical planes and a horizontal plane perpendicular to said two vertical planes, said second image located at the intersection of two perpendicular vertical planes and a horizontal plane perpendicular to said two vertical planes, wherein a subject to be tested moves said images into convergence in the center of said cubic space.

2. An electronic eye depth testing method as in claim 1 wherein said images are moved equally and in opposite directions in at least one of a series of first parallel planes using one pair of keys on a keyboard device used for controlling said images on said display screen, equally and in opposite directions in at least one of a series of second parallel planes using a second pair of keys or equally and in opposite directions in at least one of a series of third parallel planes using a third pair of keys.

3. An electronic eye depth testing method as in claim 2 wherein said series of first parallel planes is a series of horizontal planes extending through the front, rear and side walls of said cubic space.

4. An electronic eye depth testing method as in claim 3 wherein said first pair of keys on said keyboard are the left and right arrow keys.

5. An electronic eye depth testing method as in claim 2 wherein said series of second parallel planes is a series of second vertical planes extending through the top, bottom, rear and front walls of said cubic space.

6. An electronic eye depth testing method as in claim 5 wherein said second pair of keys on said keyboard are the page up and page down keys.

7. An electronic eye depth testing method as in claim 2 wherein said series of third parallel planes is a series of vertical planes extending through the bottom, top and side walls of said cubic space.

8. An electronic eye depth testing method as in claim 7 wherein said third pair of keys on said keyboard are the left and right arrow keys.

9. An electronic eye depth testing method as in claim 1 wherein only one of said images is moved in a single direction in a vertical plane using a fourth pair of keys.

10. An electronic eye depth testing method as in claim 9 wherein said fourth pair of keys on said keyboard are the delete and insert keys.

11. An electronic eye depth testing method as in claim 1 wherein only one of said images is moved in a single direction in one of said horizontal planes using a fifth pair of keys.

12. An electronic eye depth testing method as in claim 11 wherein said fifth pair of keys on said keyboard are the end and home keys.

13. An electronic eye depth testing method as in claim 1 wherein said cubic space has a vertical axis, a first horizontal axis and a second horizontal axis, said vertical axis and said first and second horizontal axes crossing as said center of said cubic space.

14. An electronic eye depth testing method as in claim 13 wherein said cubic space is rotated about said first horizontal axis by a sixth set of keys on said keyboard.

15. An electronic eye depth testing method as in claim 14 wherein said sixth set of keys are the F1 and F2 keys.

16. An electronic eye depth testing method as in claim 13 wherein said cubic space is rotated about said vertical axis by a seventh set of keys on said keyboard.

17. An electronic eye depth testing method as in claim 16 wherein said seventh set of keys are the F3 and F4 keys.

18. An electronic eye depth testing method as in claim 1 wherein said images are of like color.

19. An electronic eye depth testing method comprising a three dimensional cubic space displayed on a display screen having a first image of a three dimensional object and a second image of a three dimensional object randomly placed therewithin wherein said cubic space has a vertical axis, a first horizontal axis and a second horizontal axis, said cubic space further having a reflective surface on a rear wall parallel to said vertical axis, a reflective surface on each said side wall and on said bottom wall and said top wall and wherein said first image is reflected from each said reflective surface and said second image is reflected from each said reflective surface in a position relative to said first image and said second image respectively.

20. An electronic eye depth testing apparatus comprising a central processing unit, a display screen, an eye depth testing program, a mouse and a keyboard, said central processing unit having said eye depth testing program resident therein, said eye depth testing program displaying a three-dimensional cubic space on said display screen, said eye depth testing program displaying a first image of a three dimensional object and a second image of a three dimensional object in said cubic space on said display screen, said first and said second images randomly placed in said cubic space wherein a subject to be tested moves said images into convergence in the center of said cubic space.

* * * * *